United States Patent [19]

Hoyt et al.

[11] 3,990,441
[45] Nov. 9, 1976

[54] NEBULIZER HEATER

[75] Inventors: Edwin D. Hoyt, Hemet; Walter V. Nickmeyer, Redlands; Raymond L. Simmons, San Jacinto, all of Calif.

[73] Assignee: Rama Corporation, San Jacinto, Calif.

[22] Filed: June 9, 1975

[21] Appl. No.: 584,731

[52] U.S. Cl. .......................... 128/193; 261/DIG. 65
[51] Int. Cl.² ........................................ A61M 11/00
[58] Field of Search ........... 128/193, 192, 194, 188; 219/271, 272, 273, 275, 362, 303, 304, 305; 239/135, 338; 261/DIG. 65, 78 A, 142

[56] References Cited
UNITED STATES PATENTS

| | | | |
|---|---|---|---|
| 1,150,619 | 8/1915 | Percival et al. | 261/142 |
| 1,549,016 | 8/1925 | McLean | 219/305 |
| 1,554,219 | 9/1925 | Kitchen | 128/193 |
| 3,282,266 | 11/1966 | Walker, Jr. | 219/271 |
| 3,311,355 | 3/1967 | Rait | 261/142 |
| 3,458,948 | 8/1969 | Curtis et al. | 219/275 |
| 3,695,516 | 10/1972 | Rogers | 239/135 |

FOREIGN PATENTS OR APPLICATIONS

| | | | |
|---|---|---|---|
| 193,030 | 11/1957 | Germany | 219/305 |

*Primary Examiner*—Robert W. Michell
*Assistant Examiner*—Henry J. Recla
*Attorney, Agent, or Firm*—Georges A. Maxwell

[57] ABSTRACT

A humidifying and tempering apparatus for use in an oxygen delivery system and comprising a vessel, a supply of water in the vessel, a nebulizer in the vessel above the water, a supply of oxygen under pressure connected with the nebulizer, an elongate water conducting tube connected with the nebulizer and extending downwardly into and through the water, an elongate resistance heater element concentric within and extending longitudinally of the tube to heat that water drawn through the tube by the nebulizer to be mixed with the oxygen in the upper portion of the vessel and an oxygen delivery line communicating with the vessel above the water and conducting tempered humidified oxygen to a location for use.

6 Claims, 6 Drawing Figures

U.S. Patent  Nov. 9, 1976  Sheet 1 of 2  3,990,441
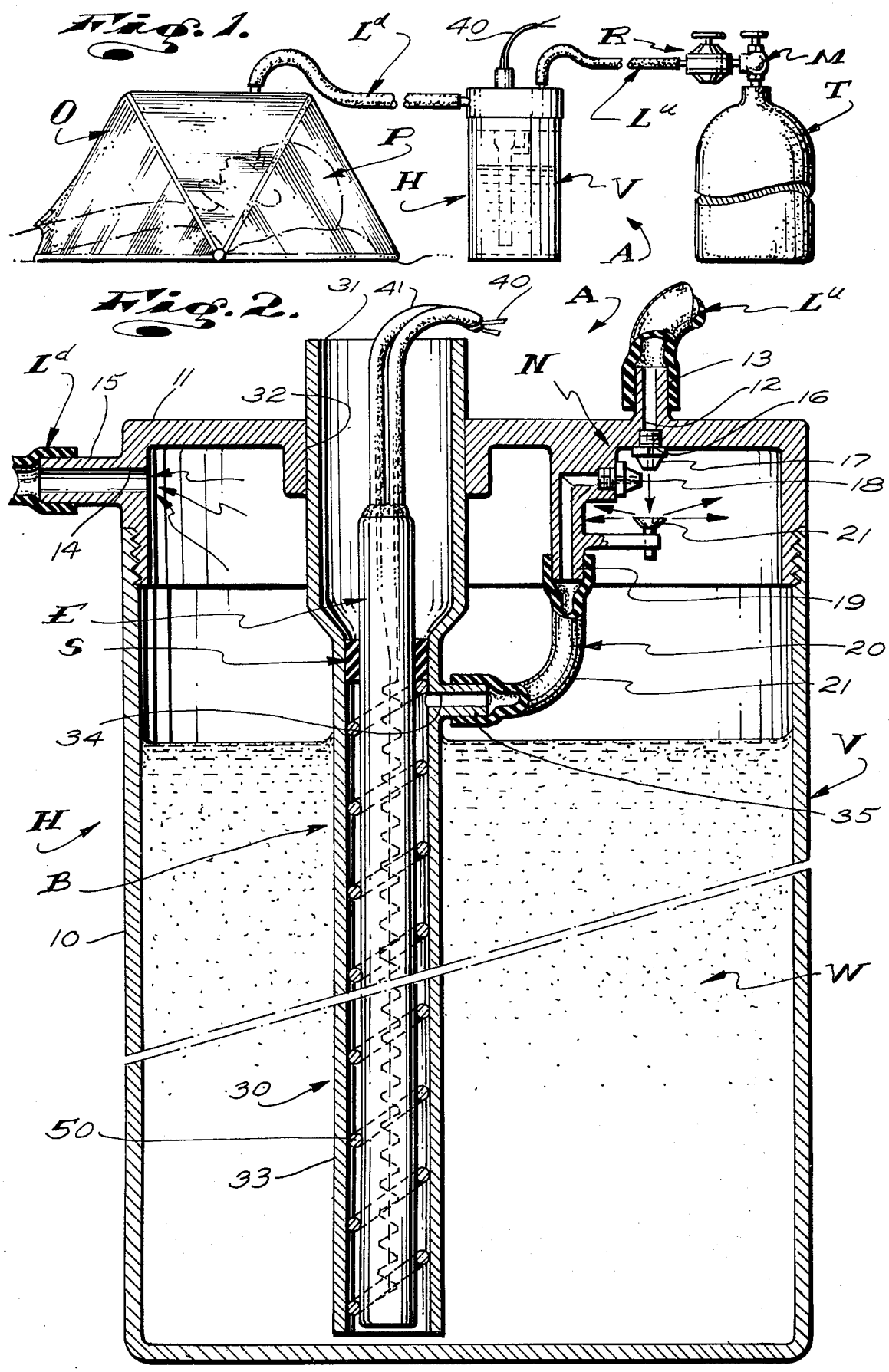

U.S. Patent  Nov. 9, 1976  Sheet 2 of 2  3,990,441
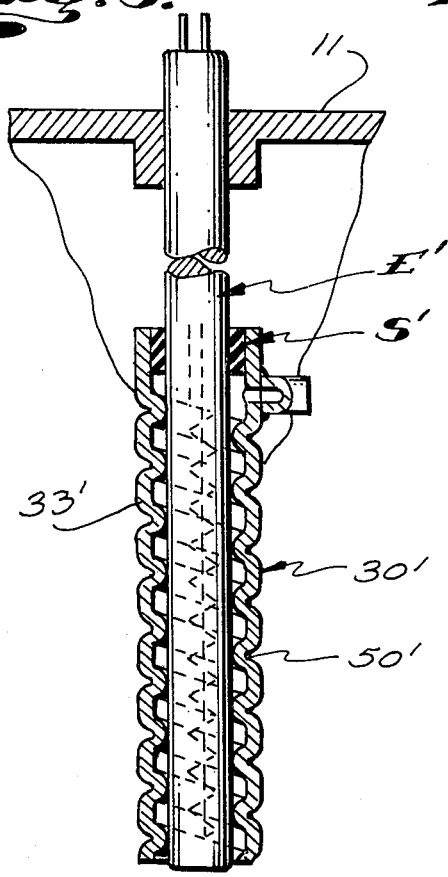
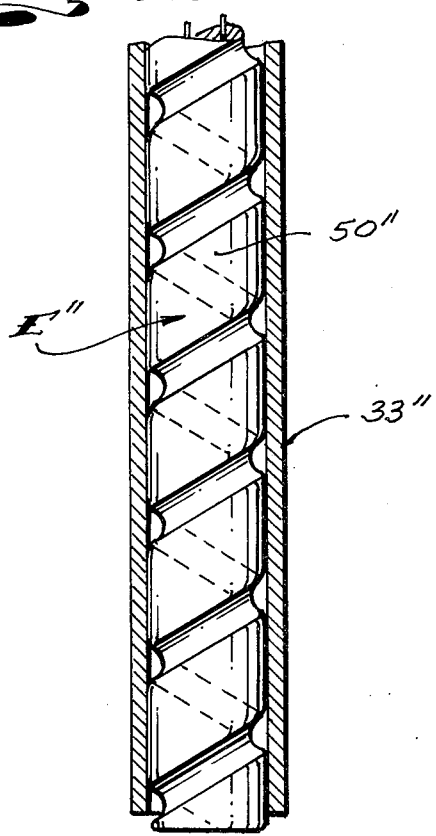
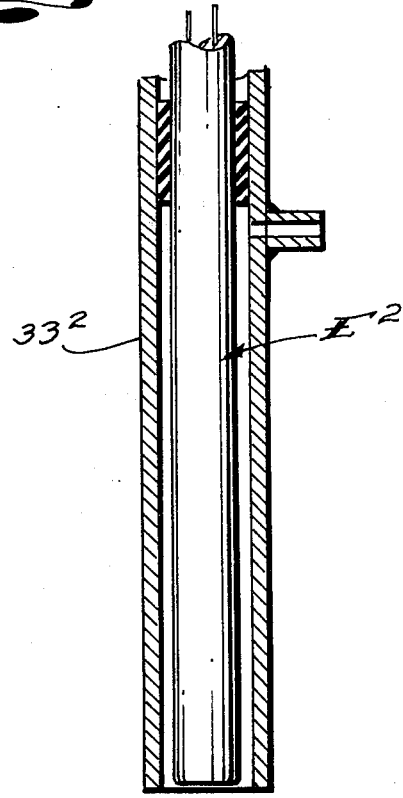
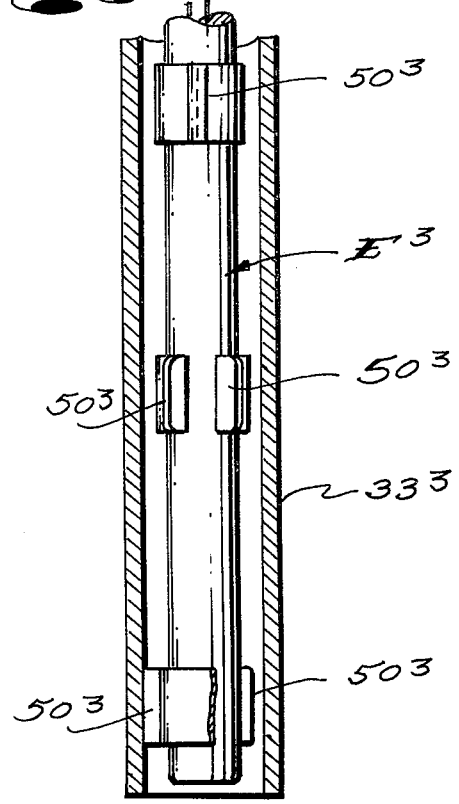

NEBULIZER HEATER

This invention has to do with novel means for humidifying and tempering oxygen in oxygen delivery means provided to deliver oxygen to persons in need of respiratory assistance or relief and is that type or class of means which is commonly referred to as a nebulizer.

It is old and well established practice in the medical art to deliver to persons requiring respiratory relief or assistance, measured volume of oxygen, to supplement the oxygen which is present and available in the ambient atmosphere. The reasons and purposes for such administration of oxygen do not affect the present invention and need not be listed or considered for the purpose of this disclosure.

The oxygen employed in the medical art for delivery to patients is supplied in tanks (often referred to as bottles or flasks) under high pressure. The oxygen thus supplied is dry and sterile and is, upon delivery to patients, relieved of pressure under control and by means of suitable outlet valves and pressure regulators related to the tanks of oxygen.

As the oxygen is relieved of pressure and is permitted to expand, it becomes cold or is chilled to a substantial extent.

In practice, it has been determined that delivery of dry oxygen, directly from supplied tanks, to patient dries and/or parches the respiratory tracts of patients causing them harm and/or great discomfort. It has been further determined that the delivery of cold or chilled oxygen to patients is subject to causing them harm and/or discomfort. As a result of the foregoing, it is common practice in the medical arts to provide humidifier means to add moisture to the oxygen and to provide heater means to temper the oxygen and/or moisture, in oxygen delivery means, whereby the above noted adverse effects can be and are effectively avoided.

The ordinary oxygen delivery means of the character here concerned with include elongate flow lines extending from the oxygen tanks or from the outlet valve and pressure regulator assemblies related to the tanks, which lines extend to suitable masks or tents related to the heads of the patients and which communicate with their mouths and/or noses.

The humidifying and heating means are, as a general rule, engaged in the flow lines. The most common and practical humidifying and heating means provided to date have involved a tank or vessel of distilled sterile water, an immersible resistance heater inserted in the supply of water in the vessel to heat the water and mixing means for mixing the heated water with the chilled oxygen.

The mixing means employed are provided in two basic forms. The most simple form of mixing means is a simple scrubber means and consists of an oxygen diffuser engaged in the vessel and serving to bubble the oxygen up and through the heated water. This scrubber type of means has been found to be wanting in many respects and is being replaced by more sophisticated atomizer or nebulizer means wherein the moving and expanding oxygen is utilized to draw heated water from the supply of water in the vessel to be broken up and mixed or combined with the oxygen.

In the above noted forms or classes of means, the water is still, most often, and as noted above, heated by an electric resistance heater entered into the vessel and submerged in the water supply therein.

Problems associated with the above noted common form of heater means are: (1) demand upon the heaters is a function of the water levels in the vessels; (2) controlling and establishing uniform water temperatures is difficult and the heaters must be cycled on and off repeatedly and at varying rates as the water levels change in the vessels; (3) heat transfer or losses through the walls of the vessels are substantial and vary so as to place added demand on the heaters; (4) high rates of power consumption are required to heat the entire volumes of water in the vessels; (5) the water must be heated to undesirably high temperatures; (6) there exists a high potential for damaging equipment as a result of overheating (as when the water levels are low and the heaters are only partially engaged in water and are cycled on to heat the small volumes of water); and (7) heater life is short due to the high operating demands imposed upon them.

It is sought to maintain the humidified oxygen as close to body temperature as is possible, that is, at 98.6° F. and to establish and maintain the relative humidity of the oxygen at 100%.

It will be apparent that in apparatuses of the character here concerned with, it is necessary that the temperature of the humidified oxygen delivered to patients be carefully controlled and that it be maintained as uniform and unvarying in temperature and relative humidity as is possible, since slight changes in temperature and humidity are readily sensed by the patients and tend to disturb their rest and raise their consciousness that they are being served by life supporting means which is often psychologically disturbing.

An object and feature of the present invention is to provide a nebulizer with improved heater means whereby the water mixed with the oxygen is heated continuously and its temperature is raised to a constant predetermined set temperature, with a minimum consumption of power.

It is another object of the invention to provide a means of the character referred to above wherein the water to be combined with the oxygen is drawn from the supply of water in a vessel through a water supply tube communicating with the venturi of a nebulizer connected with a flow line and through which the oxygen is conducted and wherein said heater means is related to said supply tube whereby only that water which is drawn from the supply of water in the vessel to the nebulizer is heated. Yet another object is to provide a tube and heater assembly of the character referred to above which includes an elongate helical divider means in an annulus between the heater and the tube and defining a longitudinally extending helical flow passage about the heater through which the water to be heated is conducted whereby controlled flow and heat transferring contact between the water and the heater is maintained to assure uniform and controlled heating of said water with minimum power demand and without cycling of the heater.

Another object and feature of this invention is to provide a structure of the character referred to wherein the vessel is closed, the nebulizer is within the vessel about the water level therein and wherein the section or portion of the flow line downstream of the nebulizer communicates with the interior of the vessel about the water level therein whereby excess water mixed with the oxygen by the nebulizer precipitates and returns to the supply of water within the vessel before the humidified oxygen enters said downstream section of the line.

Still further, it is an object and feature of the invention to provide a structure of the character referred to above wherein the heater means and nebulizer are arranged with the vessel and the supply of water and the mixed water and oxygen are contained and handled by the vessel in a manner whereby the heat generated and supplied by the heater means is efficiently utilized to temper the vessel, the water supply, the mixed together water and oxygen and the humidified oxygen in and flowing from the vessel.

It is a principal object of this invention to provide heater means of the character referred to which operates independent of and is unaffected by the water level in the vessel and an effective and dependable heater means which draws less current or has less capacity or output than is required of heaters (only if necessary) employed by the prior art to effect comparable tempering of water and oxygen in oxygen delivery systems of the character here involved.

The foregoing and other objects and features of this invention will be fully understood from the following detailed description of a typical preferred form and carrying out of the invention, throughout which description reference is made to the accompanying drawings, in which:

FIG. 1 is a diagrammatic view of an oxygen delivery apparatus embodying the present invention;

FIG. 2 is an enlarged detailed sectional view of the nebulizer and heater unit embodying the present invention and which is included in the apparatus shown in FIG. 1; and FIGS. 3, 4, 5, and 6 as partial sectional views of other forms of heating and flow tube structure which are suitable for use in carrying out the present invention.

The oxygen delivery system or apparatus A here provided includes a supply tank T of dry, sterile oxygen under high pressure, a manually adjustable outlet valve M related to the tank and a pressure regulator R connected with the outlet of the valve M. The apparatus A next includes an oxygen tent O overlying the head of a patent P to whom the oxygen is to be delivered, a humidifier H and a flow line having an upstream section $L^u$ extending between the regulator R and humidifier H and a downstream section $L^d$ extending between the humidifier H and the tent O.

It is to be understood that the tent can be replaced by a mask and a that the construction of the tent or mask can vary widely without affecting the present invention. It is also to be understood that the tank T, valve M and regulator R, illustrated in the drawings, are only intended to disclose the nature of one typical type of oxygen supply and dispensing means with which the humidifier H might be effectively related and that the specific structure illustrated is not to be considered as limiting the scope and the spirit of the invention here provided.

The humidifier H includes, generally, a vessel V, nebulizer N and heater means B.

The vessel V can vary widely in construction and is shown as including an upwardly opening tank-like bottom section or basin 10 and a cap-like closure 11, screw-threaded into and closing the open top of the basin 10. The basin 10 carries a supply of water W and is preferably established of a transparent, clear, plastic material having a low index of heat conductivity whereby the water level in the vessel can be visually monitored and a minimum of heat loss occurs through the vessel walls. The closure H is preferably molded of a suitable plastic having a low index of heat conductivity, as is the basin 10.

The closure 11 is provided with an oxygen inlet opening 12 with an outwardly projecting hose or line coupling part or projection 13 and with an oxygen outlet opening 14 with an outwardly projecting hose or line coupling part of projection 15. The opening 12 and coupling projection 13 occurs at the top of the closure and connect and communicate with the flow line section $L^u$. The opening 14 and coupling projection 15 are shown at one side of the closure and connect and communicate with the flow line section $L^d$.

In practice, and as shown, the opening 14 and the line section $L^d$ are larger in diameter than the opening 12 and line section $L^u$. This noted difference is provided since the oxygen flowing through the line section $L^u$ and through the opening 12 is compressed to a greater extent and is flowing at a faster rate than is the flow of oxygen out through the opening 14 and line section $L^d$.

The nebulizer N is preferably formed integrally with the cover 11 and is characterized by a bore 16 in the underside of the cover communicating with and extending downwardly from the opening 12. The lower end of the bore 16 accommodates a nozzle 17 directed downwardly toward and adapted to direct a jet of oxygen into the interior of the basin 10. The nebulizer N next includes a lateral port 18 in a depending tubular coupling projection 19. The port 18 is in close proximity to the nozzle 17 adjacent one side of the jet issuing from the nozzle and in that area of the nozzle and jet where a minus pressure is generated by said jet. The port 18 communicates with a flow tube 20, which tube communicates with the supply of water W in the basin 10 whereby water is drawn upwardly through the tube 20 and thence out through the port 18 by said minus pressure to join and combine with the jet of oxygen. Finally, the nebulizer includes a diffuser 21 below the nozzle 18 and port 19, in the path of the jet and upon which the jet of oxygen and the water carried thereby impinge to break up and/or atomize the water. The diffuser 21 can be a simple disc or knob supported on an arm projecting from the projection 19 on the cover, as illustrated.

The nebulizer N, described above and illustrated in the drawings, is a simple, practical and effective nebulizer. It is to be understood and is believed to be apparent that in practice, other more sophisticated nebulizer structures can be substituted for and/or used in place of the particular means N shown and described without departing from the spirit of the present invention.

In the case illustrated, the flow tube 20 is a sectional assembly and includes an upper tube section 21 with an upper end engaged with the tubular projection 19 related to the port 19 and a lower duct section communicating with the other end of the section 21 and which establishes a part or element of the heater means B, as will hereinafter be described.

The heater B provided by this invention includes an elongate, vertical, tubular metal duct 30 with an upwardly opening upper portion 31 extending through an opening 32 in the cover 11 and depending into the vessel, a lower, downwardly opening lower tube portion 33 extending downwardly into the supply of water in the basin 10 of the vessel and which terminates immediately above the bottom of the vessel or basin. The lower tube portion 33 has a lateral outlet port 34 with a tubular coupling projection 35, which projection connects with the lower end of the upper section 21 of the flow tube 20.

The portion 33 of the duct 30 establishes the lower section of the flow tube 20.

The heater B next includes an elongate cartridge type resistance heater element E arranged in an coextensive with the lower tube portion 33 of the duct. The element E has power leads 40 extending upwardly from its upper end, through and from the upper portion 31 of the duct. The power leads are arranged within a waterproof jacket structure 41 suitably formed and sealed with the upper end of the heater element.

The element E is smaller in diameter than the lower tube portion 33 of the duct in which it is arranged and cooperates therewith to establish an annular, longitudinally extending opening or fluid conducting passage.

The heater structure B next includes an annular seal S in the annular opening at the upper end of the tube portion 33 and above the port 34 to seal with the between the element E and the duct and between the upper and lower portions of the duct.

In the preferred form of the invention, the heater B includes an elongate helical divider or spacer 50 in and extending longitudinally of the annular opening defined by the element E and the tube portion 33 of the duct and cooperating with the element and the duct to define an elongate, longitudinally extending helical flow passage about the element and extending from the lower open end of the port 34 and the tube portion 33 and through which water, drawn and flowing upwardly into the flow tube and about the element E, must travel before delivery to the nebulizer N.

The spacer 50 can, as shown, be in the form of a wire wound helically about the element E and slidably engaging the interior of the duct.

It will be apparent that by adjusting the radial extent of the helical spacer 50 and by adjusting the pitch of that element, the cross-section longitudinal extent and capacity of the helical flow passage established thereby can be adjusted and set so that the maximum and most desirable and/or effective amount of contact is made by the water, flowing through the passage, with the heater element.

Further, flow director or spacer 50 is preferably established of a metal having a high index of heat conductivity and is in direct heat conducting engagement with the element E whereby the flow spacer 50 is heated and serves as a heat exchanger with the water. Still further, the tube portion 33 of the duct 30 being in heat conducting contact with the flow spacer 50 is heated and serves as a heat exchanger with the water in the duct as well as with the vapor in the vessel above the water therein.

In practice, adjustment of the output of the element to match the volume and flow rate of the oxygen and water may be accomplished by the provision and use of a simple manually operable rheostat, by the use of self regulating resistance wiring or the like.

It is to be particularly noted that since water is drawn from the bottom of the basin 10 of the vessel and is passed over the entire effective length of the heater element E, the output and/or power demand on the heater element is constant and is totally independent of the water level in the vessel and about the heater structure. Further, the vapor in the vessel above the water level therein is maintained at approximately the same temperature as the water in the vessel and no effective temperature gradient, due to the water level in the vessel, which might adversely affect the operation of the construction, is presented.

In operation, oxygen is conducted to the nebulizer under high velocity and pressure relative to the velocity and pressure of humidified oxygen flow downstream from the outlet opening 14 of the vessel. The inflowing oxygen is accelerated by the nozzle 17 of the nebulizer. The jet of oxygen issuing from the nozzle establishes a negative pressure at the port 18 and water is drawn thereby, upwardly through the duct, about the heater element, thence through the tube 20 and then out through the port 18 to combine with the jet of oxygen. The jet of oxygen and water is then diffused. The diffused jet of oxygen expands rapidly and chills, however, the water which has been previously heated by the element E, effects an immediate heat exchange which counteracts the chilling effect of the expanding oxygen. Excess water in the upper portion of the vessel drops to and recombines with the supply of water. The humidity of the oxygen in the upper portion of the vessel and which is subsequently discharged through the port 14 therein for delivery to the patient P, through the line section $L^a$, has a substantially constant relative humidity of approximately 100%.

In comparative tests, it was determined that to deliver humidified oxygen at a temperature of 98.6° F. and with a relative humidity of 100%, to the end of a line or hose leading to a patient, the temperature of the small volume of water directly heated by the element E of the present invention was a constant 118° F., whereas the temperature of the supply of water in a conventional apparatus where the entire supply of water in the vessel was heated by an immersible resistance heater was not constant and exceeded 140° F. Further, in the conventional apparatus tested, those variations in temperature of the water resulted in variations in the relative humidity of the humidified oxygen at the point of delivery to the patient. The power requirement of the tested apparatus embodying the invention did not exceed 75 watts and was constant (assuring long heater life), whereas the power requirement of the conventional test apparatus was in excess of 100 watts and was cyclical (with resulting diminished heater life expectancy).

The above test findings are only typical of many advantages attained by the present invention.

In practice, the structure of the heater means B can vary considerably without departing from the spirit of the present invention.

For example, and as shown in FIG. 3 of the drawings, duct 30' need not include the upper portion 31 provided in the first form of the invention. In such a case the element E' can be provided with an extended, inactive or cold upper portion which extends upwardly from the upper end of the duct or tube portion 33' and its related seal S', to terminate at the exterior of the vessel above the cover 11 of the vessel, substantially as shown.

In practice, the helical spacer 50 can be replaced by a radially inwardly projecting helical spacer land 50' formed in the duct 30', as shown in FIG. 3 of the drawings or can, as shown in FIG. 4 of the drawings, be established by a helical spacer land 50'' on and about the heater element E'' and defined by helical, radially outwardly opening, longitudinally extending grooves roll formed into the outer surface (sheath) of the element E''.

It is to be particularly noted and understood that the establishment of a helical flow passage in the heater means, while desirable for achieving most effective, efficient and dependable operation of the structure here provided, is not absolutely necessary or required in order to attain notable operational advantages over structure provided by the prior art.

In practice, in accordance with the above, and as shown in FIG. 5 of the drawings, the heater element $E^2$ can be arranged to extend freely through the duct or flow tube $33^2$, without spacer means to establish a helical flow passage. In such a case, the flow passage in the heater is a simple, annular passage extending longitudinally of the element $E^2$.

The principal disadvantages found in the last noted form of heater means resides in the fact the there is no direct heat conducting means between the element $E^2$ and the tube $33^2$ and most effective and efficient use of the heat generated is not assured. Further, the is a possibility that the water flowing through the annulus will establish an irregular flow pattern whereby heating of the water in a uniform and predetermined manner is not assured.

As shown in FIG. 6 of the drawings, the heater element $E^3$ can be centralized in the tube $33^3$ by longitudinally and circumferentially spaced, longitudinally extending spacer $50^3$ within the annulus and which serve as heat conductors between the element and the tube and which also serve to control the flow of water in the annulus and assure superior heat exchange between the water and the element.

The foregoing briefly noted alternate forms of heat means are shown and briefly described to illustrate a limited number of the structure variations that can be adapted in the effective carrying out of the invention.

Having described only a typical preferred form and application of the invention, I do not wish to be limited to the specific details herein set forth but wish to reserve to myself any and all modifications and variations that might appear to those skilled in the art to which the invention pertains and which fall within the scope of the following claims:

Having described our invention, we claim:

1. Humidifying and tempering apparatus for use in oxygen delivery apparatus comprising, an elongate vertical vessel with a lower water carrying portion and an upper vapor confining portion, a supply of water in the lower portion of the vessel, a nebulizer positioned in the upper portion of the vessel above the water, an oxygen supply line connected with the nebulizer and extending to a source of oxygen flowing at controlled volume and pressure, an elongate water conducting tube connected with the nebulizer and extending downwardly in the vessel into and through the water and opening adjacent the lower portion of the supply of water, an elongate resistance heater element arranged substantially concentric within and extending longitudinally of the tube in spaced relationship therewith to heat that water drawn through the tube by the nebulizer to be mixed with the oxygen in the upper portion of the vessel and an elongate oxygen delivery line communicating with the said upper portion of the vessel and conducting tempered humidified oxygen to a location for use, said vessel has an open top and includes a closure in the open top, said tube is sectional and comprises an elongated vertical metal duct with a lower portion in which the element is arranged, an upper portion engaged through the closure, a seal between the element and the upper end of the lower portion and a lateral port below the seal, said tube next comprises a tube section extending between the port of the duct and a lateral orifice of the nebulizer, said nebulizer includes an oxygen delivery nozzle on an axis substantially normal to the axis of and adjacent to the orifice and communicating with the supply line and a diffuser spaced from the nozzle and the orifice and in axial alignment with the nozzle.

2. The humidifying and tempering apparatus set forth in claim 1 wherein the heater element is smaller in diameter and is concentric within the duct whereby the element and duct cooperate to define an annular flow passage extending longitudinally of and about the heater element whereby water is moved substantially continuously and uniformly about the heater element in heat transferring contact therewith as oxygen is delivered to the nebulizer and in independent of the volume and level of water in the vessel.

3. The humidifier and tempering apparatus set forth in claim 1 including an elongated helical between the duct and the heater element and defining an elongate helical water conducting flow passage between the duct and element through which the water flowing through the duct and about the element is directed.

4. The humidifier and tempering apparatus set forth in claim 3 wherein the spacer includes a radially inwardly projecting helical rib form in the duct and engaging the element.

5. The humidifier and tempering apparatus set forth in claim 1 wherein said element is formed with an elongate radially outwardly opening and longitudinally extending helical groove defining a duct engaging helical land, said groove and duct defining a helical water conducting flow passage extending about and longitudinally of the element.

6. The humidifier and tempering apparatus set forth in claim 1 including centralizing and flow directing means between the duct and the element, and comprising elongate circumferentially spaced flow directing vanes extending longitudinally of and between and in bearing contact with the element and the duct between the port in and through the open lower end of the duct.

* * * * *